US011285108B1

(12) United States Patent
Brañes Oshima et al.

(10) Patent No.: US 11,285,108 B1
(45) Date of Patent: Mar. 29, 2022

(54) PHYTOSTEROLS FOR THE PREVENTION OR TREATMENT OF NON-ALCOHOLIC STEATOHEPATITIS

(71) Applicant: Naturalis S.A., Santiago (CL)

(72) Inventors: Mariá Cecilia Brañes Oshima, Santiago (CL); Thomas Haack, Santiago (CL); Thomas Härting Glade, Santiago (CL)

(73) Assignee: Naturalis S.A., Santiago (CL)

( * ) Notice: Subject to any disclaimer, the term of this patent is extended or adjusted under 35 U.S.C. 154(b) by 0 days.

(21) Appl. No.: 17/196,715

(22) Filed: Mar. 9, 2021

(51) Int. Cl.
| | |
|---|---|
| *A61K 9/16* | (2006.01) |
| *A61K 9/00* | (2006.01) |
| *A61P 1/16* | (2006.01) |
| *A61K 9/08* | (2006.01) |
| *A61K 31/575* | (2006.01) |

(52) U.S. Cl.
CPC .............. *A61K 9/16* (2013.01); *A61K 9/0053* (2013.01); *A61K 9/08* (2013.01); *A61K 31/575* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 6,129,944 | A | 10/2000 | Tiainen et al. |
| 9,629,378 | B2 | 4/2017 | Harting Glade et al. |

FOREIGN PATENT DOCUMENTS

| | | |
|---|---|---|
| EP | 1 142 494 A | 10/2001 |
| WO | 98/58554 A1 | 12/1998 |
| WO | 2013/081462 A1 | 6/2013 |

OTHER PUBLICATIONS

CAS SciFinder abstract (database CAPLUS Acc. No. 2019:1052487) of Sanchez-Crisostomo et al., Current Pharmaceutical Biotechnology (2019), 20(3), pp. 197-214.*
Nutrartis brochure [online]. "Nutrartis. For a better life, the best sterols. Wellness Inside." Nutrartis S.A., 2020. [retrieved on May 9, 2021]. Retrieved from the Internet: <URL: www.nutrartis.com/wp-content/uploads/2020/06/Nutrartis_brochure1_ingles_NE_V103_mail_L.pdf>.*
Sanchez-Crisostomo et al., Current Pharmaceutical Biotechnology (2019), 20(3), pp. 197-214.*
Ex Parte Frederic Batteux and Bernard Weill (Appeal 2007-0622), Informative Opinion issued Mar. 27, 2007.*
Chen, D. et al. "Phytosterols increase circulating endothelial progenitor cells and insulin-like growth factor-1 levels in patients with nonalcoholic fatty liver disease: A randomized crossover study", Journal of Functional Foods, 13:148-157 (2015).
Dillman, J. et al., "Quantitative Liver MRI-Biopsy Correlation in Pediatric and Young Adult Patients With Nonalcoholic Fatty Liver Disease: Can One Be Used to Predict the Other?", AM J Roentgenol., 210(1): 166-174 (2018).
Drori, A. et al., "Oral Administration of CardioAid and Lunasin Alleviates Liver Damage in a High-Fat Diet Nonalcoholic Steatohepatitis Model", Digestion, 96: 110-118 (2017).
Javanmardi, M. et al., "Effects of Phytosterol Supplementation on Serum Levels of Lipid Profiles, Liver Enzymes, Inflammatory Markers, Adiponectin, and Leptin in Patients Affected by Nonalcoholic Fatty Liver Disease: A Double-Blind, Placebo-Controlled Randomized Clinical Trial", Journal of the American College of Nutrition, 1-8 (2018).
Kleiner, D. et al., "Design and Validation of a Histological Scoring System for Nonalcoholic Fatty Liver Disease", Hepatology, 41(6): 1313-1321 (2005).
Song, L. et al., "Phytosterol esters attenuate hepatic steatosis in rats with non-alcoholic fatty liver disease rats fed a high-fat diet", Scientific Reports, 1-14 (2017).
Song, L. et al., "Combined effect of n-3 fatty acids and phytosterol esters on alleviating hepatic steatosis in non-alcoholic fatty liver disease subjects: a double-blind placebo-controlled clinical trial", British Journal of Nutrition, 123: 1148-1158 (2020).
Cicero et al., "Short-Term Effects of a Combined Nutraceutical on Lipid Level, Fatty Liver Biomarkers, Hemodynamic Parmeters, and Estimated Cardiovascular Disease Risk: A Double-Blind, Placebo-Controlled Randomized Clinical Trial," Adv Ther, 2017, 34:1966-1975.
Patel et al., "Association of Noninvasive Quantitative Decline in Liver Fat Content on MRI with Histologic Response in Nonalcoholic Steatohepatitis," Ther Adv Gastroenterol, 2016, 9151:692-701.
Plat et al., "Protective Role of Plant Sterol and Stanol Esters in Live Inflammation: Insights from Mice and Humans," PLOS ONE, 2014, 9(10):e110758, pp. 1-11.
Shaghagi et al., "Water Dispersible Plant Sterol Formulation Shows Improved Effect on Lipid Profile Compared to Plant Sterol Ester,s" Journal of Functional Foods, 2014, 6:280-289.

* cited by examiner

*Primary Examiner* — Brian J Davis
(74) *Attorney, Agent, or Firm* — Merchant & Gould P.C.

(57) ABSTRACT

The present disclosure provides compositions and methods for preventing or treating non-alcoholic steatohepatitis. The composition comprises phytosterol particles, and at least a portion of the phytosterol particles have a size of less about 1 micron. The method comprises administering orally a daily dose of at least about 2 g of phytosterol comprising free phytosterol particles having a size less than about 1 micron. Both animal model studies and human trial studies confirmed the effectiveness of the compositions and methods.

5 Claims, 4 Drawing Sheets

PHYTOSTEROLS FOR THE PREVENTION OR TREATMENT OF NON-ALCOHOLIC STEATOHEPATITIS

INTRODUCTION

Non-alcoholic fatty liver disease (NAFLD) is the buildup of extra fat in liver cells that is not caused by alcohol. It is normal for the liver to contain some fat. However, if more than 5% of the liver weight is fat, then it is called fatty liver or steatosis. However, a liver is still considered healthy up to 10% of fat content by the total weight of the liver.

The most severe form of NAFLD is called non-alcoholic steatohepatitis (NASH). NASH causes the liver to swell and become damaged. The full spectrum of liver lesions in NASH include steatosis, inflammation, and fibrosis. To classify the full spectrum of liver lesions in NAFLD, the NAFLD Activity Score (NAS) was developed. (Kleiner et al. Hepatology 41: 1313-21, 2005). Kleiner et al. is hereby incorporated by reference in its entirety.

NAFLD Activity Score (NAS) associates a semi quantitative value to four main histological features, which are steatosis (0-3 score range) for indicating fat accumulation, hepatocellular ballooning (0-2 score range) as a marker of cell injury, lobular inflammation (0-2 score range) as assessment of inflammatory foci, and fibrosis state (0-2 score range). If the sum of the four scores is three or more (>3), it is considered NASH.

NASH is closely related to the triple epidemic of obesity, pre-diabetes, and diabetes. The symptoms of NASH are often invisible until the liver is damaged beyond repair. The risk factors for NASH are hypertension, heart disease, high blood lipid levels, insulin resistance, type 2 diabetes, and obesity. The increasing rates of obesity and comorbidities such as metabolic syndrome manifested among others by high serum triglycerides (TG), low serum high-density lipoprotein cholesterol (HDL-C), and diabetes have boosted NAFLD prevalence to around 25% of the population worldwide. The relationship with the above-mentioned comorbidities, has driven a panel of experts to redefine the term NAFLD to MAFLD, for metabolic (dysfunction) associated fatty liver disease, considered a more appropriate name that better reflects the current knowledge. As yet no pharmacological treatment has been approved, NASH progression to more severe clinical stages is becoming the most common indication for liver transplantation.

Some nutraceuticals such as phytosterols, which encompass both plant sterols and stanols, have been suggested to alleviate NAFLD condition particularly because they may control some of the altered parameters in the lipid profile of humans, and consequently they may reduce liver inflammation.

WO 2013/081462 discloses the use of phytosterol in the prevention or treatment of hepatic inflammation in human regardless of the origin of the inflammation, be it part of NASH symptoms, alcoholic liver disease, hepatitis A, B or C. However, the animals used in the model study were fed with fatty diet and showed liver inflammation only, which by itself is not NASH. Therefore their disclosure of the effect of phytosterol on hepatic inflammation is not indicative of the effectiveness of phytosterol for the prevention or treatment of NASH.

Chen et al. (Journal of Functional Foods 13, 2015, 148-157) and Javanmardi et al. (Journal of the American College of Nutrition, DOI: 10.1080/07315724.2018.1466739) carried out clinical studies in NAFLD patients diagnosed by ultrasonography using commercial mixtures of free plant sterols and stanols. Though both described a significant effect on the reduction of low-density lipoprotein cholesterol (LDL-C), insulin resistance, and inflammatory plasma parameters, no reduction in plasma triglyceride (TG) could be observed, and no control of liver status was reported.

Song et al. (1) (The British Journal of Nutrition, 123(10), 2020, 1148-1158) reported that after testing a protocol with an arm consisting of a 12-week-long administration of phytosterol esters to NAFLD patients, results of liver computed tomography demonstrated that liver fat content was increased. By contrast, Song et al. (2) (Scientific Reports, 7 Feb. 2017, 7:41604, DOI: 10.1038/srep41604) also reports that phytosterol esters were able to attenuate hepatic steatosis in rats. Apparently, Song et al. (1) and Song et al. (2) showed that the results in experiments with animal models cannot necessarily be extrapolated to humans.

Drori et al. (Digestion 2017; 96:110-118) studied Lunasin, a soy derived peptide with anti-inflammatory properties and CARDIOAID™ (Archer Daniels Midland Company, Chicago, Ill.) plant sterols derived from vegetable oils to determine their immunomodulatory effects in mice fed with high fat diet, as animal model of NASH. However, the scores of NAS, hepatic ballooning and hepatic inflammation in the high fat diet control group (no treatment) and the group with CARDIOAID™ were found identical, as shown in FIG. 2b. Therefore, CARDIOAID™ had no positive effect on alleviating in an animal model the deleterious effect of high fat diet.

It is highly desirable effective compositions and methods for preventing or treating NASH or NAFLD particularly in human subjects.

Phytosterols for the Prevention or Treatment of Non-Alcoholic Steatohepatitis The present disclosure relates to the use of compositions comprising free phytosterol particles having a size of sub-micron for the prevention or treatment of non-alcoholic steatohepatitis in human subjects.

There is a growing interest in determining the possible usefulness of compositions comprising phytosterol in the prevention or treatment of NAFLD in patients. However, as shown in the introduction of the present disclosure this has not yet been proven.

WO 2013/081462 discloses a preference for small size phytosterol particles, quoting the techniques for particle size reduction disclosed in U.S. Pat. No. 6,129,944, WO 98/58554, and EP 1142494, but none of techniques disclosed yield particles of sub-micron size.

In particular, U.S. Pat. No. 6,129,944 shows the particle size distribution of microcrystalline plant sterols produced by pulverization ranging from 2 to 7 microns, with the percentage of particles between 2 and 2.5 microns varying from less than about 1 to about 12%. WO 98/58554 shows the preparation of pulverized plant sterol by jet-pulverizing and impact milling, wherein the particle size varied from 2 to over 100 microns, with the percentage of particles between 2 and 2.5 microns varying from negligible to 22%. EP 1142494 shows the preparation of a micro milled plant sterol emulsifier dispersion, claiming average particle sizes "of about 1 to about 40 microns," but Examples of EP 1142494 show particle sizes from 10 to 20 microns.

ADM (Archer Daniels Midland Company) elaborates a variety of plant sterol product such as CARDIOAID-XF advertised as ultra-fine powder with 95% minimum sterol content. The catalogue of the product indicates a mean particle size of 15 microns.

Therefore, to one skilled in the art it is evident that phytosterol compositions used in WO 2013/081462, were composed of phytosterol particles larger than 1 micron.

In some aspects, the present disclosure relates to a composition comprising phytosterol particles, wherein at least a portion of the phytosterol particles have a size less than about 1 micron. In embodiments, a cumulative particle number percentage of phytosterol particles having a size less than 1 micron in the composition is in a range from about 10% to about 100%, or from about 30% to about 95%, or from about 40% to about 90%, or from about 50% to about 80%, or from about 60% to about 70%. In embodiments, a cumulative particle number percentage of phytosterol particles having a size less than 1 micron in the composition is at least about 10%, or least about 30%, or at least about 40%, or at least about 50%, or at least about 60%, or at least about 70%, or at least about 80%, or at least about 90%, or at least about 95%, or at least about 99%. In embodiments, the present composition consists essentially of phytosterol particles having a size less than about 1 micron.

In some embodiments, the phytosterol of the present disclosure comprise at least 70 wt. %, or at least 80 wt. %, or at least 90 wt. %, or at least 95 wt. %, or at least 99 wt. % of beta-sitosterol, based on the total weight of the phytosterol particles. In embodiments, the phytosterol consist essentially of beta-sitosterol.

In some aspects, the present disclosure relates to a method of preventing or treating non-alcoholic steatohepatitis in human subjects comprising administering orally a daily dose of at least about 2 g of phytosterol comprising free phytosterol particles, wherein a cumulative particle number percentage of free phytosterol particles having a size less than about 1 micron is in a range from about 10% to about 100%, or from about 30% to about 95%, or from about 40% to about 90%, or from about 50% to about 80%, or from about 60% to about 70%. In embodiments, the method of the present disclosure comprises administering orally a daily dose of at least about 2 g of phytosterol comprising free phytosterol particles, wherein a cumulative particle number percentage of the phytosterol particles having a size less than about 1 micron is at least about 10%, or least about 30%, or at least about 40%, or at least about 50%, or at least about 60%, or at least about 70%, or at least about 80%, or at least about 90%, or at least about 95%, or at least about 99%.

In some embodiments of the method according to the present disclosure, the phytosterol comprise at least 70 wt. %, or at least 80 wt. %, or at least 90 wt. %, or at least 95 wt. %, or at least 99 wt. % of beta-sitosterol, based on the total weight of the phytosterol. In embodiments of the present method, the phytosterol consist essentially of beta-sitosterol.

In some embodiments of the method according to the present disclosure, the phytosterol is a solid composition. In certain embodiments of the present method, the solid composition is in the form of capsule, tablet, or dragee.

In some embodiments of the method according to the present disclosure, the phytosterol is a liquid composition.

The present compositions and methods provide a number of advantages in preventing or treating NASH. For example, the animal model studies were carried out with C57Bl6 mice, the most widely utilized animal model, and the Chilean rodent *Octogon degus* (commonly known as Degu). Degu, different from mice, possesses the cholesteryl ester transfer protein (CETP), an enzyme involved in the exchange of cholesteryl esters for triglycerides between HDL and LDL, which makes its lipid metabolism closer to human, as compared to that of mice. The animal mode study is therefore more indicative of effectiveness in treating NASH in human.

The present disclosure also provides a year-long clinical trial with thirty NASH volunteers, 20 women and 10 men. Subjects were asked to maintain their life style and feeding habits and to include one sachet of Cardiosmile dispersed in one glass of water. A sachet contains 10 ml of dispersion comprising 2 g of particles of free phytosterol with a size of sub-micron. At the start and the end of the year period, liver steatosis was quantified by Magnetic Resonance Imaging Proton Density Fat Fraction (MRI-PDFF). The trial proved the effectiveness of the phytosterol dispersion in the treatment of non-alcoholic steatosis in human.

Definitions

As used herein, "weight percent," "wt %," "percent by weight," "% by weight," and variations thereof refer to the concentration of a substance as the weight of that substance divided by the total weight of the composition and multiplied by 100.

As used herein, "cumulative particle number percentage" of particles having a size less than about 1 micron (or sub-micron) means the sum of the percent (or fraction) of particles finer than about 1 micron in a given composition.

As used herein, "g" represents gram; "L" represents liter; "mg" represents "milligram ($10^{-3}$ gram);" "mL" represents milliliter ($10^{-3}$ liter); "dL" represents deciliter ($10^{-1}$ liter); "nm" represents nanometer ($10^{-9}$ meter); micron or micrometer is $10^{-6}$ meter. As used herein, "sub-micron" refers to a number less than about 1 micron.

As used herein, the units "mg/100 g," "mg/100 mL," "mg/dL,", "g/L," or "mg/L" are units of concentration or content of a component in a composition. One "mg/L" equals to one ppm (part per million). One Da equals to one g/mol. The unit of temperature used herein is degree Celsius (° C.).

As used herein, "IU" is an International Unit, which is a unit of measurement for the amount of a substance; the mass or volume that constitutes one international unit varies based on which substance is being measured, and the variance is based on the biological activity or effect, for the purpose of comparison across substances.

As used herein, a value of "p25" or "p75" (or any value from 0-100) describes the value (or score) below which 25% or 75% of the observations may be found.

The term "about" is used in conjunction with numeric values to include normal variations in measurements as expected by persons skilled in the art, and is understood to have the same meaning as "approximately" and to cover a typical margin of error, such as ±10% of the stated value. The term "about" also encompasses amounts that differ due to different equilibrium conditions for a composition resulting from a particular initial composition. Whether or not modified by the term "about," the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes having two or more compounds that are either the same or different from each other. It should also be noted that the term "or" is generally employed in its sense including "and/or" unless the content clearly dictates otherwise.

In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

The term "substantially free" may refer to any component that the composition of the disclosure lacks or mostly lacks. When referring to "substantially free" it is intended that the component is not intentionally added to compositions of the disclosure. Use of the term "substantially free" of a component allows for trace amounts of that component to be included in compositions of the disclosure because they are present in another component. However, it is recognized that only trace or de minimis amounts of a component will be allowed when the composition is said to be "substantially free" of that component. Moreover, the term if a composition is said to be "substantially free" of a component, if the component is present in trace or de minimis amounts it is understood that it will not affect the effectiveness of the composition. It is understood that if an ingredient is not expressly included herein or its possible inclusion is not stated herein, the disclosure composition may be substantially free of that ingredient. Likewise, the express inclusion of an ingredient allows for its express exclusion thereby allowing a composition to be substantially free of that expressly stated ingredient.

The methods and compositions of the present disclosure may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

"AST" represents Aspartate Aminotransferase; "ALT" represents Alanine Aminotransferase; "BMI" (Body Mass Index) is a person's weight in kilograms divided by the square of height in meters; "TG" represents triglycerides; "GGT" represents Gamma-Glutamyl Transpeptidase; "LDL cholesterol" represents Low-density lipoprotein cholesterol.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure. In the following description, various embodiments of the present disclosure are described with reference to the following drawings, in which.

DETAILED DESCRIPTION

Figure 1:
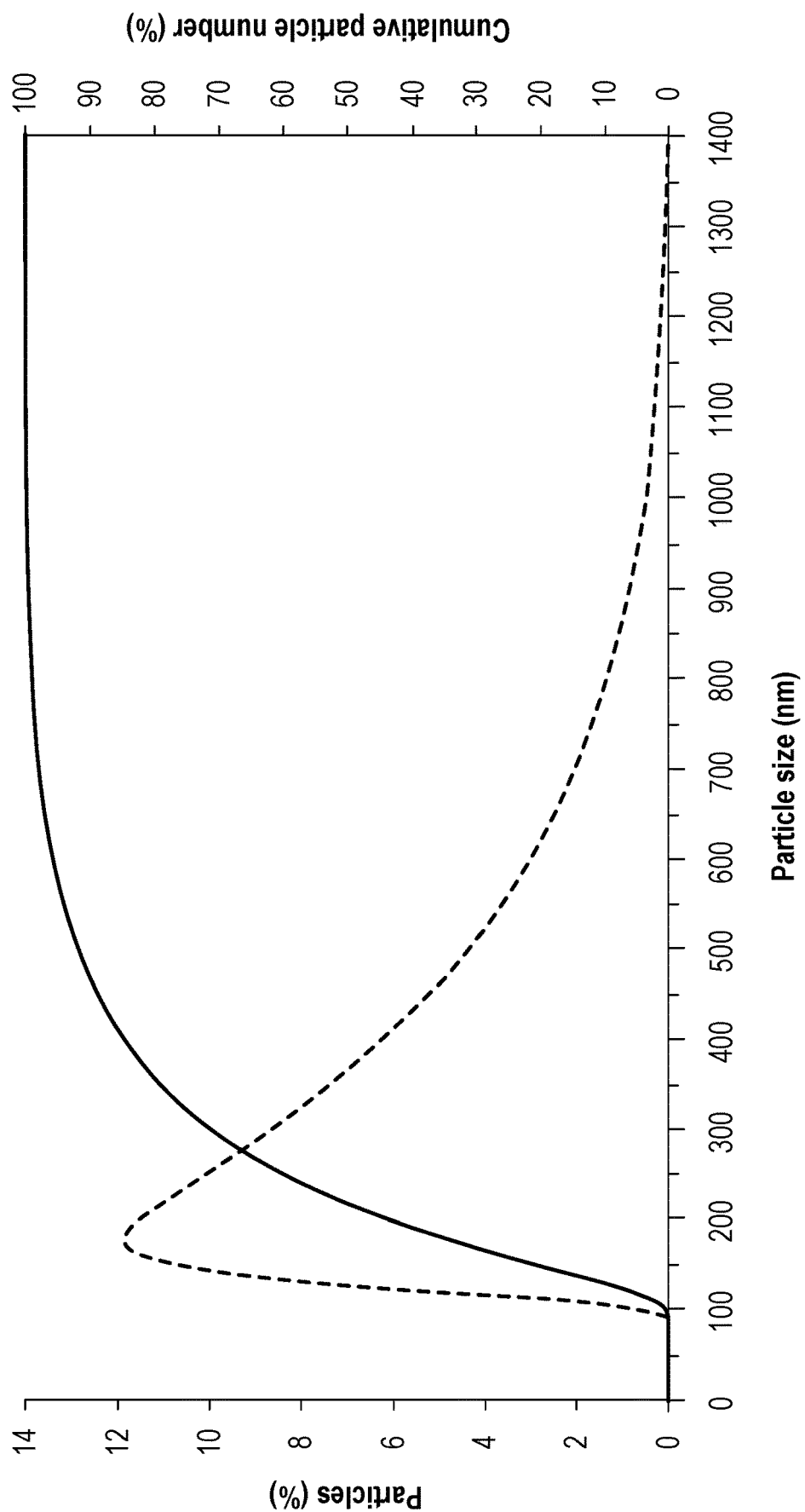
FIG. 1 shows the particle size distribution of phytosterol particles in Cardiosmile as an embodiment composition.

The present disclosure provides a method for the prevention or treatment of non-alcoholic steatohepatitis. The method comprises administering compositions comprising free phytosterol particles having a size of sub-micron.

Prevention means that a composition according to the invention is administered to a subject who is at risk of developing NASH so as to avoid its development. Treatment means that a composition according to the invention is administered to a subject with the aim to diminish fat content in at least about 30% relative to baseline or/and that the liver returns as much as possible to a healthy condition. For treatment as well as for prevention ingestion is the preferred means of supplementation.

WO 2013081462 discloses a preference for small size phytosterol particles, quoting the techniques for particle size reduction disclosed in U.S. Pat. No. 6,129,944, WO 9858554, and EP 1142494, but none of the disclosed techniques yield particles of sub-micron size.

U.S. Pat. No. 6,129,944 shows the particle size distribution of microcrystalline plant sterols produced by pulverization ranging from 2 to 7 microns, with the percentage of particles between 2 and 2.5 microns varying from less than about 1 to about 12%. WO 98/58554 shows the preparation of pulverized plant sterol by jet-pulverizing and impact milling, wherein the particle size varied from 2 to over 100 microns, with the percentage of particles between 2 and 2.5 microns varying from negligible to 22%. EP 1142494 shows the preparation of a micro milled plant sterol emulsifier dispersion, claiming average particle sizes "of about 1 to about 40 microns," but Examples of EP 1142494 show particle sizes from 10 to 20 microns.

ADM (Archer Daniels Midland Company) elaborates a variety of plant sterol product such as CARDIOAID-XF advertised as ultra-fine powder with 95% minimum sterol content. The catalogue of the product indicates a mean particle size of 15 microns.

Therefore, to one skilled in the art it is evident that phytosterol compositions used in WO 2013/081462, were composed of phytosterol particles larger than 1 micron.

In some aspects, the present disclosure relates to a composition comprising phytosterol particles, wherein at least a portion of the particles have a size less than about 1 micron. In embodiments, the cumulative particle number percentage of phytosterol particles having a size less than 1 micron in the composition is in a range from about 10% to about 100%, or from about 30% to about 95%, or from about 40% to about 90%, or from about 50% to about 80%, or from about 60% to about 70%. In embodiments, the cumulative particle number percentage of phytosterol particles having a size less than 1 micron in the composition is at least about 10%, or least about 30%, or at least about 40%, or at least about 50%, or at least about 60%, or at least about 70%, or at least about 80%, or at least about 90%, or at least about 95%, or at least about 99%.

In some embodiments, the phytosterol particles of the present disclosure comprise at least 70 wt. %, or at least 80 wt. %, or at least 90 wt. %, or at least 95 wt. %, or at least 99 wt. % of beta-sitosterol, based on the total weight of the phytosterol particles.

In some aspects, the present disclosure relates to a method of preventing or treating non-alcoholic steatohepatitis in human subjects comprising administering orally a daily dose of at least about 2 g of phytosterol comprising free phytosterol particles, wherein the cumulative number percentage of free phytosterol particles having a size less than about 1 micron is in a range from about 10% to about 100%, or from about 30% to about 95%, or from about 40% to about 90%, or from about 50% to about 80%, or from about 60% to about 70%. In embodiments, the method of the present disclosure comprises administering orally a daily dose of at least about 2 g of phytosterol comprising free phytosterol particles, wherein the cumulative number percentage of free phytosterol particles having a size less than about 1 micron is at least about 10%, or least about 30%, or at least about 40%, or at least about 50%, or at least about 60%, or at least about 70%, or at least about 80%, or at least about 90%, or at least about 95%, or at least about 99%.

In some embodiments of the method according to the present disclosure, the phytosterol comprise at least 70 wt. %, or at least 80 wt. %, or at least 90 wt. %, or at least 95 wt. %, or at least 99 wt. % of beta-sitosterol, based on the total weight of the phytosterol.

In some embodiments of the method according to the present disclosure, the phytosterol is a solid composition. In certain embodiments, the solid composition is in the form of capsule, tablet, or dragee.

In some embodiments of the method according to the present disclosure, the phytosterol is a liquid composition.

In the present disclosure, it has been found that surprisingly, compositions comprising sub-micron size particles of phytosterol are significantly more effective for the prevention or treatment of non-alcoholic steatohepatitis. To this effect, such compositions comprise at least about 10% of phytosterol particles with a size of sub-micron, preferably at least about 50% of phytosterol particles with a size of sub-micron, and most preferably at least about 95% of phytosterol particles with a size of sub-micron, wherein, percentage refers to the cumulative percentage number of phytosterol particles having a size of sub-micron.

Experiments in animals and human volunteers were carried out with compositions comprising free phytosterol particles with a size of sub-micron. In some embodiments, the compositions were obtained from commercial sources, for example, Cardiosmile, which is known to comprises an aqueous dispersion of free phytosterol particles with a size of sub-micron. In other embodiments, the compositions comprise dry phytosterol particles with a size of sub-micron, which were obtained by spray drying Cardiosmile.

The intake of the dispersion by human subjects was very effective in NASH patients and helpful for the prevention or treatment of non-alcoholic steatosis.

As shown in FIG. 1, the phytosterol particles in Cardiosmile consist almost entirely of particles with a size of sub-micron.

Figure 2:
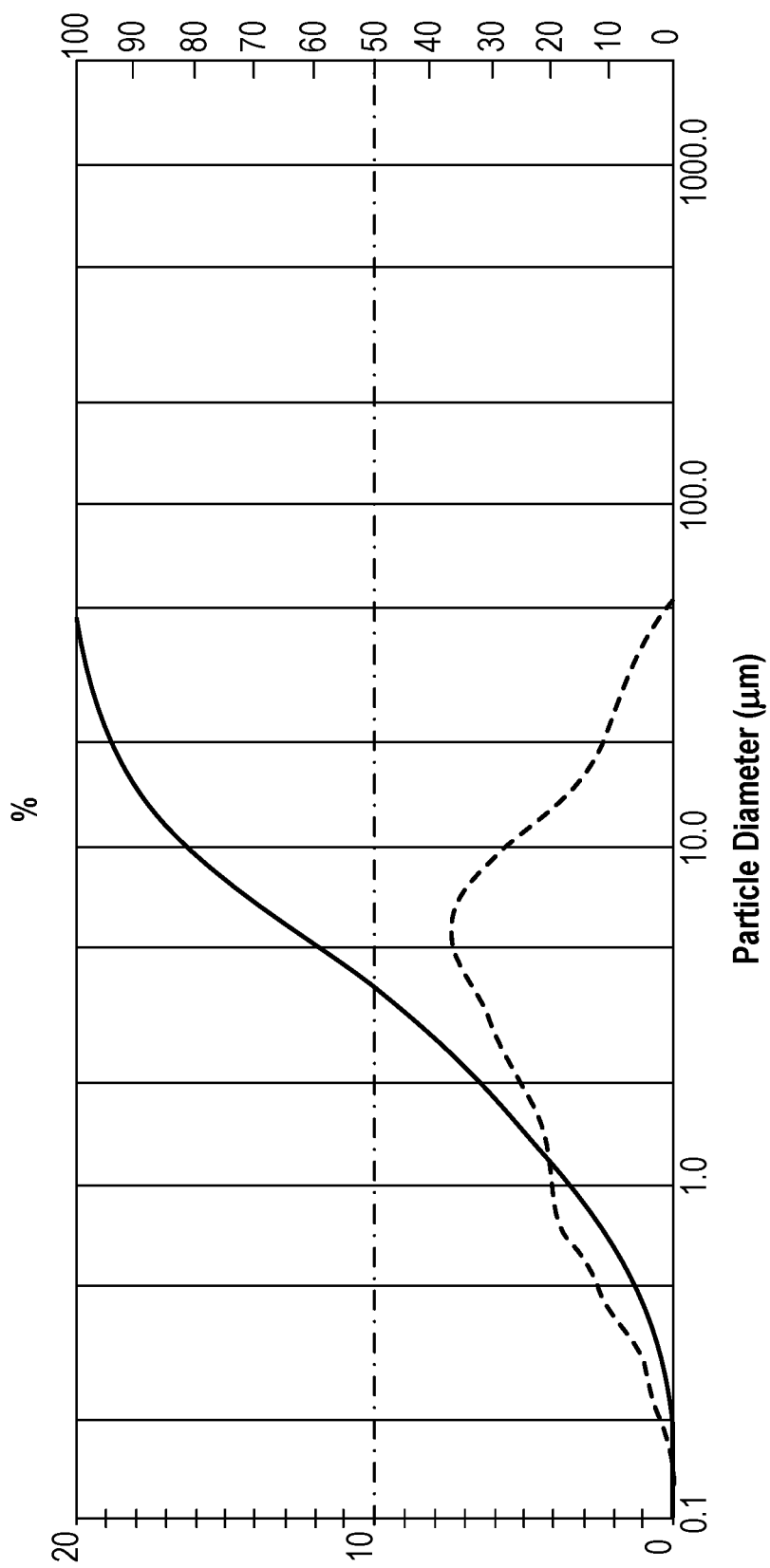
FIG. 2 shows the particle size distribution of an embodiment composition comprising dry phytosterol particles obtained by spray drying Cardiosmile, corresponding to the plot of the data of Table 1.
Figure 3:
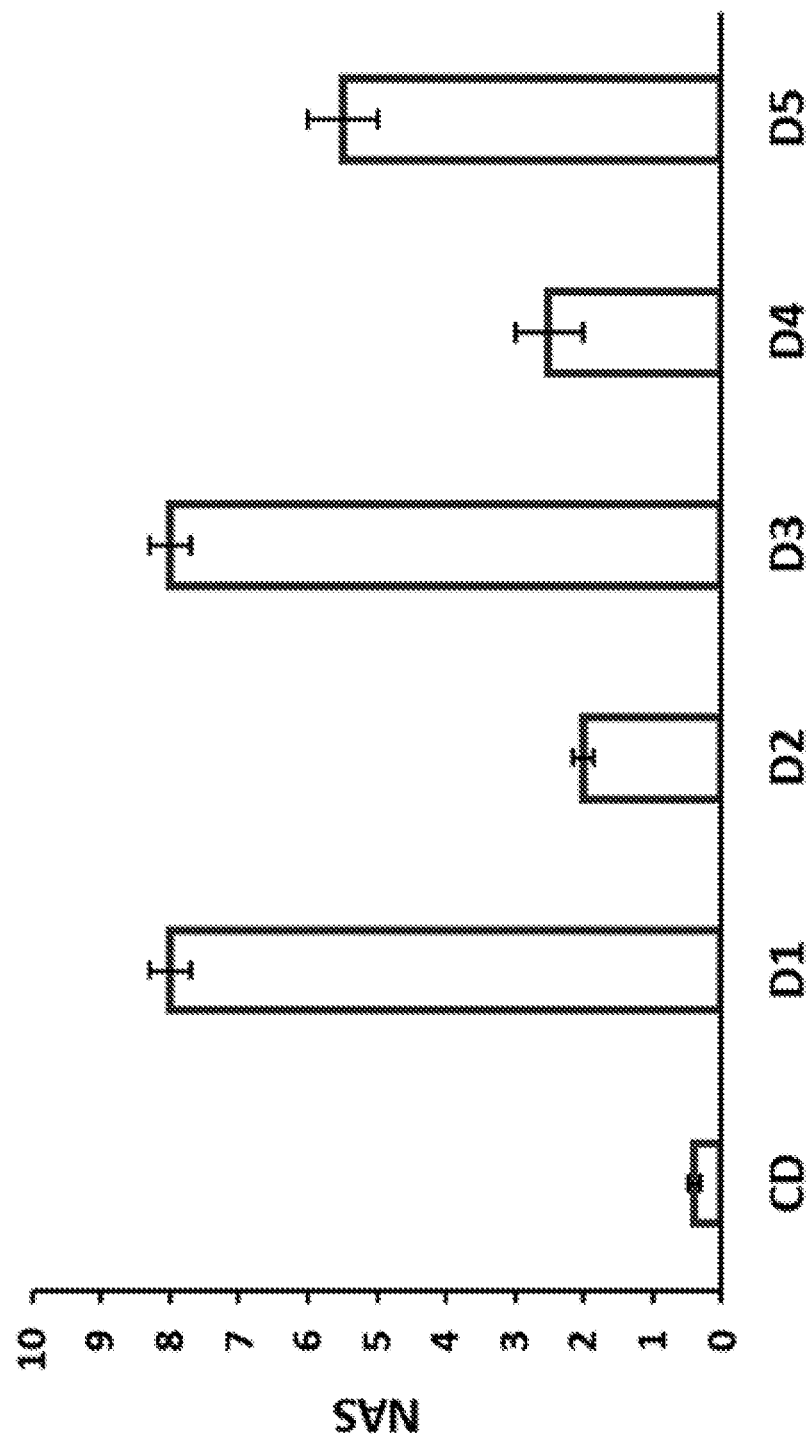
FIG. 3 shows the results of NAFLD Activity Score (NAS)±SEM for the different diets utilized in Example 1.

Table 1 shows the particle size distribution of an embodiment composition comprising dry free phytosterol particles obtained by spray drying Cardiosmile. Apparently, around 17% of the particles have a size below 1 micron. FIG. 2 corresponds to the plot of the data of Table 1. Particle size distributions were determined with a laser diffraction particle size analyzer MALVERN INSTRUMENTS, MSX1 in the "Materials characterization service division" of the "Department of nuclear materials" Chilean Nuclear Energy Commission (CCHEN).

TABLE 1

Particle size distribution of an embodiment composition comprising dry free phytosterol particles obtained by spray drying Cardiosmile.

| Size (Low) µm | Result in % | Size (High) µm | Result Below % | Size (Low) µm | Result in % | Size (High) µm | Result Below % |
|---|---|---|---|---|---|---|---|
| 0.10 | 0.00 | 0.12 | 0.00 | 2.83 | 6.16 | 3.49 | 47.19 |
| 0.12 | 0.06 | 0.15 | 0.06 | 3.49 | 6.67 | 4.30 | 53.87 |
| 0.15 | 0.19 | 0.19 | 0.25 | 4.30 | 7.14 | 5.29 | 61.01 |
| 0.19 | 0.41 | 0.23 | 0.66 | 5.29 | 7.32 | 6.52 | 68.34 |
| 0.23 | 0.73 | 0.28 | 1.39 | 6.52 | 7.00 | 8.04 | 75.33 |
| 0.28 | 1.17 | 0.35 | 2.56 | 8.04 | 6.13 | 9.91 | 81.46 |
| 0.35 | 1.73 | 0.43 | 4.29 | 9.91 | 4.92 | 12.21 | 86.38 |
| 0.43 | 2.38 | 0.53 | 6.68 | 12.21 | 3.73 | 15.04 | 90.11 |
| 0.53 | 3.05 | 0.66 | 9.72 | 15.04 | 2.84 | 18.54 | 92.95 |
| 0.66 | 3.61 | 0.81 | 13.34 | 18.54 | 2.25 | 22.84 | 95.19 |
| 0.81 | 3.97 | 1.00 | 17.30 | 22.84 | 1.86 | 28.15 | 97.06 |
| 1.00 | 4.07 | 1.23 | 21.38 | 28.15 | 1.52 | 34.69 | 98.58 |
| 1.23 | 4.19 | 1.51 | 25.56 | 34.69 | 1.02 | 42.75 | 99.60 |
| 1.51 | 4.62 | 1.86 | 30.18 | 42.75 | 0.40 | 52.68 | 100.00 |
| 1.86 | 5.20 | 2.30 | 35.38 | 52.68 | 0.00 | 64.92 | 100.00 |
| 2.30 | 5.66 | 2.83 | 41.04 | 64.92 | 0.00 | 80.00 | 100.00 |

Cardiosmile is an aqueous dispersion comprising up to 25% free phytosterol elaborated according to the method disclosed in U.S. Pat. No. 9,629,378. Cardiosmile was elaborated with the product ARBORIS® Sterols AS-2® (Arboris LLC, Savannah, Ga.), which is a mixture of sterols and stanols derived from pine trees including but not limited to brassicasterol, campesterol, campestanol, stigmasterol, beta-sitosterol, beta-sitostanol and D5 avenasterol, with a total sterol content of at least 99%. Beta-sitosterol is the main component, ranging from 70 to 80%, based on the total weight of sterols and stanols. The commercial product Arboris® Sterols AS-2® has the appearance of a white to off white free flowing prills or fines. Arboris® Sterols AS-2® are large size sterol crystals.

However, other sterol-based products can be utilized to produce aqueous dispersions of phytosterol particles with a size of sub-micron, with a particle size distribution similar to that shown in FIG. 1, with whatever single phytosterol or phytosterol mixture regardless of their origin.

Both Cardiosmile and the spray dried Cardiosmile powder were effective in treating NASH. Cardiosmile can be conveniently added to drinking water, soda, milk, dairy drinks, yogurt, etc., while the most convenient form of administering the dried powder is in the form of tablets, dragees or capsules with suitable excipients to allow for a short disintegration time.

The animals were fed with different compositions or diets comprising phytosterol particles including the commercial product Cardiosmile and free dry phytosterols obtained by spray drying of Cardiosmile. Then, animals under anesthesia were euthanized and liver histology was utilized to quantify NAS in degus and in mice. The trials with animal models proved the effectiveness of the diet comprising Cardiosmile and of the diet comprising dehydrated Cardiosmile as well, in preventing NASH.

As shown in Example 1, mice fed Cardiosmile containing diets, as evidenced by the low value of NAS, repaired overall histological features related to NASH induced in mice fed with high fat diet, and it has been unexpectedly found that, spray dried Cardiosmile containing diet, was also capable of repairing overall histological features related to NASH in mice fed with high fat diet. Human trial study detailed in Example 3 also proved the effectiveness of the present compositions and methods in treating NASH in human.

EXAMPLES

Certain embodiments of the present disclosure are further described with reference to the following examples. These examples are intended to be merely illustrative of the disclosure and are not intended to limit or restrict the scope of the present disclosure in any way and should not be construed as providing conditions, parameters, reagents, or starting materials that must be utilized exclusively in order to practice the art of the present disclosure.

Example 1: NASH Recovery by Treatment with Cardiosmile and Spray Dried Cardiosmile Powder Various diets containing phytosterol particles were prepared according Table 2. For elaboration of supplemented diets, D1 was grinded and each phytosterol formulation was incorporated under continuous agitation until a homogeneous mixture is formed. Water was added in a sufficient amount to form a moldable dough. Cylinders of about 1 cm diameter were then gently dehydrated in a vacuum oven at 40° C. until constant weight was achieved. D3 was prepared by mixing D1 with an aqueous suspension of ARBORIS® Sterols AS-2®, the raw material for elaborating Cardiosmile. D4 was prepared by mixing D1 with an aqueous suspension of dry phytosterol. D5: phytosterol esters were first melted and then mixed with the same weight amount of grinded D1. The process was repeated until all D1 was homogeneously included and then dough formation was proceeded as with others.

TABLE 2

Diets containing phytosterol particles used in Example 1.

| | |
|---|---|
| D1 | Atherogenic diet, (57 BB TestDiet) 1.2% cholesterol, 56% of energy from fat |
| D2 | D1 + 2% of free phytosterol from Cardiosmile |
| D3 | D1 + 2% of ARBORIS$^R$ Sterols AS-2$^R$ |
| D4 | D1 + 2% free phytosterol from spray dried Cardiosmile. |
| D5 | D1 + 3.3% phytosterol esters (Vitasterol S-80) |
| CD | Control diet (5015 LabDiet) |

C57B16 male mice weighing around 13.7±0.7 g and maintained at 22±3° C. and humidity of 50-60%, under dark/light cycles of 12-12 hours having free access to drinking water and CD food were put in the groups described below (n=15 in each) and were fed for 30 days with D1. After that period of time, mice were divided in 5 groups, 15 animals each. One group kept fed with D1, but the other 4 groups were fed with D2, D3, D4 and D5 respectively. A sixth group was kept on feeding during all experimental period with CD. After one month, mice under anesthesia were euthanized and liver histological sections stained with hematoxylin eosin were analyzed for NAFLD Activity Score (NAS) determination. D1 diet generated a massive accumulation of fat, hepatocyte ballooning and lobular inflammation leading to NASH. D2 diet had high efficacy in liver recovery, and almost no fat accumulation was detected, closely followed by D4. Hepatocyte morphology was almost normal and much less ballooning was observed with both diets. Leukocyte infiltration was decreased but not yet abolished with D2 nor with D4. D5 showed partial efficacy only and D3 maintained all NASH characteristics produced by D1 administration.

Example 1 shows that Cardiosmile and dry phytosterol obtained from Cardiosmile repaired overall liver histological features related to NASH in mice fed with high fat diet.

Example 2: Prevention of NASH Formation by Cardiosmile in *Octodon degus*

Various diets containing phytosterol particles were prepared according Table 3, in a similar manner to the diets of Example 1.

TABLE 3

Diets containing phytosterol particles used in Example 2.

| | |
|---|---|
| D1 | D4 + 3.3% of sterol esters (Vitasterol S-80) |
| D2 | D4 + 2% of ARBORIS$^R$ Sterols AS-2$^R$ |
| D3 | D4 + 2% free phytosterol from Cardiosmile. |
| D4 | Test Diet 58Y1, DIO Rodent Purified Diet with 60% Energy from fat |
| CD | Control diet (P5 rabbit, Champion, Chile) |

Female adults *Octodon degus*, weighing around 200±20 g and maintained at 22±3° C. and humidity of 50-60%, under dark/light cycles of 12-12 hours having free access to drinking water and rabbit conventional food were put in the groups described below (n=15 in each).

Each group was administered a single diet either CD or D1 or D2 or D3 or D4 during a four-week period. After that period of time, *Octodon degus* under anesthesia were euthanized and liver histology was analyzed after hematoxylin eosin staining. The average NAFLD activity score (NAS) ±SEM was graphed.

Figure 4:
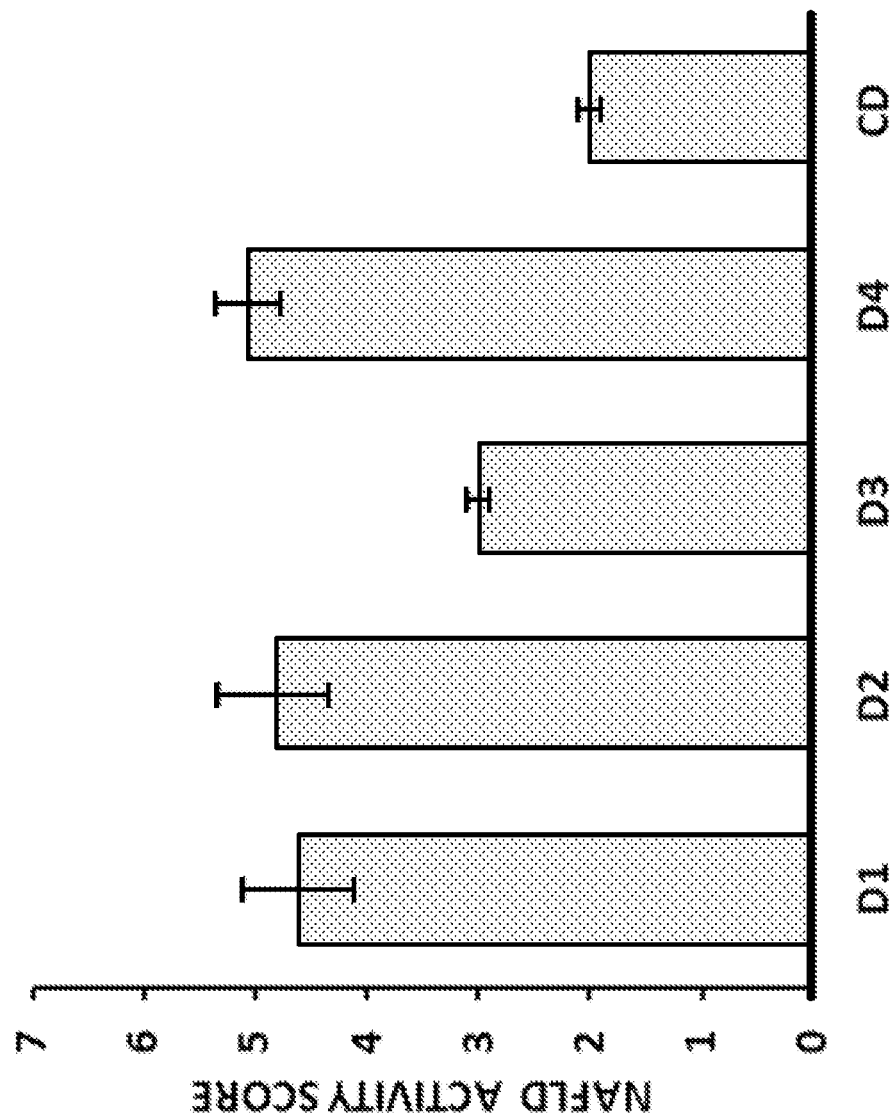
FIG. 4 shows the NAS results for the different diets utilized in Example 2.

As shown in FIG. 4, D4 induced NASH as demonstrated by the more than 150% increase in NAS with respect to a control diet. D1, the diet with esterified sterols, and D2, the diet with free phytosterol of ARBORIS® Sterols AS-2®, were not able to prevent NASH development produced by high fat diet. Nevertheless, D3 successfully prevented the detrimental effect of D4, the high fat diet, on liver. In average, NAS did not overpass the limit of 3, considered the threshold of NASH.

Example 2 proved that Cardiosmile prevents NASH in *Octodon degus* fed with high fat diet.

Example 3: Human Trial with Cardiosmile

Volunteers between 19 and 90 years old with fat body measured by Dual Energy X-ray Absorptiometry or DEXA>25% for men and >30% for women, an average liver steatosis between 17.4% and 35% quantified by MM PDFF that had not been previously diagnosed of NASH o NAFLD nor had been under treatment for any liver disease or weight management were treated in this example. In addition, volunteers should have at least one of the following characteristics:

Hypertriglyceridemia (triglycerides >150 mg/dL and <499 mg/dL)
Hypercholesterolemia (total cholesterol >200 mg/dL)
Type 2 diabetes and/or hypertension
CRPus>1 mg/L.
AST or ALT>twice normal value Pregnant women or people with cirrhosis, chronic liver diseases, other liver pathologies, cancer, hemochromatosis, Wilson disease, fasting glucose of more than 126 mg/dl or ALT>300 U/L, were excluded. People taking phytosterols or any of the following treatments in the previous 3 months, were also rejected: metformin, thiazolidinediones, vitamin E, UDCA (Ursodeoxycholic acid), SAM-e (Sadenosylmethionine), betaine, milk thistle, gemfibrozil, anti-TNF therapies, probiotics.

Thirty final volunteers, 20 women and 10 men were selected and were asked to maintain their life style and feeding habits and to include during one year the consumption of one sachet of Cardiosmile (10 ml of aqueous dispersion comprising 2 g of ARBORIS® Sterols AS-2®) dispersed in one glass of water before lunch. By the end of the year, liver steatosis was checked by MRI PDFF. Although liver biopsy is the gold standard for diagnosing NASH, it is not indicated in all patients with suspected disease. It is invasive, expensive and not without risk. In support of the use of MRI as a valuable technique to quantify liver fat and predict NASH, Dillman et al. has shown that over 15% of liver fat determined by MM, liver fat correlates with biopsy confirmed patients with NASH. (Dillman et al. Am J Roentgenol. (2018) 210(1): 166-174.)

As depicted in Table 4, more than 75% participants were obese, had high plasma TG and a moderate liver steatosis, consistent with our inclusion criteria for NASH.

TABLE 4

Baseline characteristics of subjects included in the trial

| | Age (years) | BMI | Liver fat (%) | TG (mg/dl) | LDL-c (mg/dl) | ALT (IU/l) | AST (IU/l) | GGT (IU/l) |
|---|---|---|---|---|---|---|---|---|
| Median | 54.5 | 32.9 | 20 | 168.5 | 127 | 35 | 32 | 31 |
| p25; | 48; | 31; | 18; | 145; | 98; | 34; | 27; | 24; |
| p75 | 61 | 35 | 22 | 237 | 153 | 64 | 41 | 37 |

Table 5 shows the results after one-year treatment with Cardiosmile. After one-year treatment with Cardiosmile all parameters were reduced but, the relative reduction of liver fat content with respect to baseline conditions was most consistently detected in all patients and clinically relevant. In addition, liver enzymes and lipids in plasma were also reduced.

TABLE 5

Relative change between baseline and one-year treatment with daily ingestion of one sachet of Cardiosmile.

| | BMI | Liver fat (%) | TG (mg/dl) | LDL-c (mg/dl) | ALT (IU/l) | AST (IU/l) | GGT (IU/l) |
|---|---|---|---|---|---|---|---|
| Median | -4% | -30% | -20% | -8% | -12% | -10% | -13% |
| p25; p75 | -5%; 1% | -42%; -8% | -33%; 5% | -27%; 7% | -39%; -9% | -37%; -2% | -18%; 1% |

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of treating non-alcoholic steatohepatitis in human subjects diagnosed with non-alcoholic steatohepatitis (NASH), the method comprising administering orally a daily dose of at least about 2 g of phytosterol comprising free phytosterol particles, wherein a cumulative number percentage of the free phytosterol particles having a size less than about 1 micron is in a range from about 10% to about 100%, or from about 30% to about 95%, or from about 40% to about 90%, or from about 50% to about 80%, or from about 60% to about 70%.

2. The method according to claim 1, wherein the cumulative number percentage of free phytosterol particles having a size less than about 1 micron is at least about 10%, or least about 30%, or at least about 40%, or at least about 50%, or at least about 60%, or at least about 70%, or at least about 80%, or at least about 90%, or at least about 95%, or at least about 99%.

3. The method according to claim 1, wherein the phytosterol is a solid composition.

4. The method according to claim 3, wherein the solid composition is in the form of capsule, tablet or dragee.

5. The method according to claim 1, wherein the phytosterol is a liquid composition.

* * * * *